United States Patent [19]

Van't Hooft et al.

[11] Patent Number: 5,084,001
[45] Date of Patent: Jan. 28, 1992

[54] METHOD AND APPARATUS FOR EFFECTING RADIOACTIVE THERAPY IN AN ANIMAL BODY

[75] Inventors: Eric Van't Hooft, Gezichtslaan 16, 3956 BB Leersum; Libbe Van Zwol, Veenendaal, both of Netherlands

[73] Assignee: Eric Van't Hooft, Leersum, Netherlands

[21] Appl. No.: 564,526

[22] Filed: Aug. 9, 1990

Related U.S. Application Data

[63] Continuation-in-part of Ser. No. 436,877, Nov. 15, 1989, Pat. No. 5,030,194, which is a continuation-in-part of Ser. No. 71,835, Jul. 10, 1987, Pat. No. 4,881,937.

[30] Foreign Application Priority Data

Jul. 10, 1986 [NL] Netherlands .................. 8601808

[51] Int. Cl.⁵ .................... A61N 5/00; A61M 37/04
[52] U.S. Cl. ............................ 600/3; 600/7; 250/497.1
[58] Field of Search .................... 600/1, 3, 6, 7; 250/497.1

[56] References Cited

U.S. PATENT DOCUMENTS 4,851,694  7/1989  Rague et al. .................. 250/497.1
4,881,937  10/1989  Hooft et al. .................. 600/3
5,030,194  7/1991  Hooft .......................... 600/7

FOREIGN PATENT DOCUMENTS 0152124  8/1985  European Pat. Off. .......... 600/7
0158630  10/1985  European Pat. Off. .......... 600/7
1466774  7/1973  Fed. Rep. of Germany ...... 600/1
3643893  6/1988  Fed. Rep. of Germany ...... 600/7

Primary Examiner—Lee S. Cohen
Assistant Examiner—Krista M. Pfaffle
Attorney, Agent, or Firm—Griffin, Branigan & Butler

[57] ABSTRACT

A method and apparatus for effecting radiation therapy by placing at least one guide tube through an orifice in an animal body and disposing the end portion of the guide tube near the site of intended therapy. The other end of the guide tube is connected to a channel in a shielding block. A high dose radiation source assembly is moved from the channel to the end portion and positioned a plurality of times at each of a series of preselected positions lying in the end portion to effect a plurality of pulsed radiations. The effects of low dose radiation can be duplicated by the high dose radiation source, the radiation field can be patterned, and when the repeated pulsed radiations are within repair times of healthy cells, cancer cells are destroyed and healthy cells survive.

35 Claims, 2 Drawing Sheets

METHOD AND APPARATUS FOR EFFECTING RADIOACTIVE THERAPY IN AN ANIMAL BODY

This is a continuation-in-part of U.S. patent application Ser. No. 436,877, filed on Nov. 15, 1989, now U.S. Pat. No. 5,030,194, which application is in turn a continuation-in-part of U.S. patent application Ser. No. 071,835, filed on July 10, 1987, U.S. Pat. No. 4,881,937, the entire disclosures of which are incorporated herein by reference and relied upon for disclosure herein.

The present invention relates to apparatus and method for effecting radiation therapy in an animal body, e.g. a human, and more particularly to such treatment conducted with apparatus generally known as after-loading devices.

FIELD OF INVENTION

As is well known in the art, localized malignancies may be effectively treated with radiation emitted from a discrete radioactive source placed near that malignancy, which is commonly referred to as brachytherapy. The effective treatment, however is dependent upon the particular malignancy, the position of the malignancy in the body, the activity of the radioactive source, and the positions of and the accuracy of positioning the radioactive source at or near the malignancy. Such treatments involve an intrusion into the animal body, e.g. human body, and that intrusion may be through a natural orifice in the body, if the malignancy so admits, or through a surgically provided orifice, e.g. by way of implant needles and other special devices positioned at the malignancy. In either case, the effectiveness of the treatment depends, to a large measure, on selected positions of the radioactive source and upon accurately placing the radioactive source at the selected positions near the malignancy. With some malignancies, a single radioactive source positioning may be sufficient for effective treatment, but with other malignancies, multiple radioactive source positioning in and around the malignancy, may be required. In addition, with such multiple positioning of the radioactive source or sources, the amount of radiation for effective treatment may vary with the different positions of the radioactive sources, and therefore, specific regimens of treatment are often necessary in terms of both the positioning of the radioactive source or sources and the duration of radiation exposure to the malignancy.

Since the radioactive sources used in such treatment can constitute a hazard to a person administering the treatment, devices are now commercially available which allow the positioning of the radioactive source and the treatment therewith in the patient with minimum radiation exposure to the person or with no exposure whatsoever. These devices allow the positioning of and treatment with the radioactive source in the patient after the person administering the treatment moves away from the patient. In other words, the radioactive source is loaded into the patient for treatment after the person leaves the patient, and these devices are, therefore, generally referred to as "after-loading devices".

Generally speaking, the radioactive sources used with these after-loading devices fall into two major categories. The first category is that of a low dose rate (LDR) source capable of providing radiation of about 25 to 100 cGy/Hr with sources of up to about 0.5 curies, and the second category is that of a high dose rate (HDR) source capable of providing radiation of greater than about 30 cGy/minute with sources of about 7 curies or more. Medium dose rate (MDR) sources are also available, but these fall, generally, between the characteristics of LDR and HDR sources. However, since MDR sources require substantially the same handling precautions as HDR sources, for purposes of the present specification an HDR source is herein defined to include MDR sources. An LDR source emits low levels of radiation and can be safely in proximity to the person carrying out the treatment for short periods of time. An HDR source emits higher doses of radiation and cannot be safely used in proximity to that person, even for relatively short periods of time. The after-loading devices for use of these two different radioactive sources are thus divided into two categories of machines, i.e. a low dose rate (LDR) machine and a high dose rate (HDR) machine.

In the prior art, an LDR machine is, generally, operated by driving a transport means, e.g. a flexible cable, with an LDR source from a safe (e.g. radiation shielding block), through a guide tube and to the site of intended therapy in the patient. The correct positioning of the LDR source for effective LDR source therapy is achieved in various manners in the prior art, but the most usual manner is as follows. An applicator, e.g. an implant needle, is positioned by a physician, sometimes surgically, and the correct positioning of that applicator is confirmed by X-ray or fluoroscopic procedures. Thereafter, the patient is moved to a shielded treatment room and the applicator is connected, by appropriate connectors, to an LDR machine. The assumption is that the LDR machine will correctly move the LDR source to the applicator and the LDR source will be reasonably accurately positioned in the applicator. By use of appropriate excursion measuring devices, normally associated with an LDR machine, such assumptions are generally justified. This assumption is further justified since effective treatment with an LDR source often spans many hours, e.g. 20 or 30 or even 50 or 70 hours. In view of this length of continuous treatment in a patient, very accurate continued positioning of the LDR source, opposite the malignancy, is not always possible, but the assumption is that the positioning of the source is reasonably accurate.

However, the above assumptions are not always correct and incorrectly positioned LDR sources may result. This results in less effective or ineffective therapy and, in addition, may unnecessarily expose healthy tissue to radiation. Thus, this procedure is less than desirable.

In addition, it is often necessary to employ multiple LDR sources at different sites around the general site of intended therapy, even when treating a single localized malignancy, since a single LDR source does not emit sufficient radiation over sufficient area or volume to effectively treat many, even localized, malignancies. In such case, the same procedure described above is used for each different site of intended therapy, and any of the above-noted inaccuracies will be compounded.

An LDR source assembly is usually in the form of a flexible ribbon, e.g. plastic ribbon, in which are embedded a plurality of spaced apart discrete radioactive LDR sources. The source ribbon is prepared in lengths, as specified by the physician so as to contain the number of discrete sources determined by a physician to be appropriate for treatment of a specific site of intended therapy for an individual patient. For treatment of an individual patient, a number of sites of intended therapy may be selected by the physician and, hence, a number of sections of source ribbon will be used in such treatment. Since these sections of source ribbon are prepared for treatment of specific sites of a specific patient, they cannot be normally used for treating a different patient and must be discarded after treatment.

In a typical application, the section of ribbon may be from 0.5 to 10 or more centimeters in length and contain 1 to 10 discrete, spaced apart radioactive sources. For example, when 5 discrete, spaced apart radioactive sources are in the section of ribbon, these are, in effect, 5 separate points of radiation, and for treating some malignancies these multiple points of radiation are an advantage.

With high dose rate (HDR) machines, the HDR source is too radioactive for use in proximity to the person administering the treatment, in the manner of the LDR machine. In the prior art, the HDR machines are, generally, operated by placing an implant at the correct position for effective therapy and driving a single HDR source from its channel, through a guide tube until the HDR source is in the correct position in the implant. Various devices have been described in the prior art for determining when the HDR source reaches that correct position in the implant. However, these prior art devices lack desired accuracy, and this desired accuracy is even more of a disadvantage in HDR machines, since exposure of the malignancy to radiation is often only in terms of minutes, e.g. 10, 15 or 20 minutes, and a small inaccuracy in positioning the HDR source can result in large inaccuracies in effective treatment, in view of the short times involved.

As used by the prior art, the single HDR source cannot duplicate the separate points of radiation, as described above in connection with the LDR machine, and these separate points of radiation can be of advantage in some treatments, as noted above. On the other hand, the LDR source ribbon cannot be reused, as noted above, and treatment with an LDR source requires long and uncomfortable treatment times for the patient, along with lack of desired accuracy in positioning the LDR source, as noted above. Hence, while both of these methods of treatments have advantages and disadvantages, neither is entirely as satisfactory as would be desired.

BACKGROUND OF THE INVENTION

In a first improvement disclosed in the above-mentioned parent applications, a test assembly is disposed in a separate test channel in a safe, e.g. shielding block. A connector tube connects at a first end to the test channel and at a second end to a connector disposed in the guide tube. Thus, a juncture is formed at the connector between the guide tube and the connector tube. A test assembly transport thread (cable) is attached at one end to the test assembly and at another end to a test assembly drive means for driving the test assembly from the test channel, through the connector tube and connector, and toward the second end of the guide tube. In this arrangement, the source assembly and the test assembly are alternatingly drivable toward the second end of the guide tube. A detector means is provided for detecting the presence of a test assembly or the source assembly in the guide tube between the juncture and the second end of the guide tube.

Thus, in this arrangement, the test assembly is driven through the connector tube and guide tube and past the detector, which is generally at the juncture between the connector tube and the guide tube. The detector will determine when the test assembly passes that juncture. Since the guide tube between the juncture and the site of intended therapy will be a common path for both the test assembly and the source assembly, accurately measuring the excursion of the test assembly from the detector to the site of intended therapy (confirmed by X-ray or the like) will give a very precise measurement of the excursion necessary for the source assembly once that source assembly also passes the detector and into the common pathway guide tube. The guide tube can remain essentially in place on the patient during both when the test assembly is operated and when the source assembly is operated, and, hence, disturbing the common pathway guide tube is not necessary. This gives a very precise positioning of the source assembly for effective radiation therapy and is a substantial improvement over the prior art.

In the second improvement disclosed in the parent applications, the test assembly may, in fact, be an LDR source. With this change, the LDR source may be used for the test assembly or may be used for radioactive therapy, although a single LDR source would have very limited practical clinical application for treating cancers. However, the LDR source can be effectively used as a test for radiation. For example, an LDR source may be placed in an applicator for treating uterine cancer (at a position intended to be occupied by a HDR source during treatment), and a radiation probe can be placed in the rectum to measure the radiation of the LDR source at the rectum (which should be the minimum possible). This radiation can then be ratioed to the radiation which will be received by the rectum when the HDR source is at that position. This can be of considerable assistance to the physician in determining and confirming proper positions for the HDR source.

In another aspect of the parent applications, in order to allow multiple sites of intended therapy to be serviced by a single machine, an indexer means, which is known to the art, may be disposed between the juncture (the juncture of the guide tube and the connector tube) and the second end of the guide tube so as to provide a plurality of branched guide tubes extending from the indexer to a plurality of sites of intended therapy. With this arrangement, for example, the correct positioning of the HDR source in any one of the branched guide tubes may be determined by using the LDR source as the test assembly, as described above, and after that correct positioning is determined, the HDR source is serially passed through each of the plurality of guide tubes, in turn, so that the source is positioned serially at different sites of intended therapy around and about the malignancy. By choosing a particular residence time of the HDR source at each position in each of the branched guide tubes, the total radiation provided by the HDR source, with a short residence time in each position, can be somewhat equivalent to the radiation provided by a plurality of LDR sources with much longer residence times. In serially passing the HDR source through the plurality of branched guide tubes, a wide area in and around the malignancy can be radiated to effect similar radiation to that which would have been achieved with a conventional LDR machine using a plurality of LDR sources.

BRIEF DESCRIPTION OF THE INVENTION

The present invention provides yet a further improvement. In one aspect of the present invention, a method is provided wherein an HDR machine, using an HDR source, can essentially duplicate the separate points of radiation provided by an LDR machine using a plurality of discrete LDR sources disposed in lengths of LDR ribbon. In this method, at least one guide tube is placed through at least one orifice in the body such that an end portion of the guide tube (which end portion will have a length somewhat the same as that of the length of a usual LDR ribbon source assembly) is disposed near the site of intended therapy. The other end of the guide tube is connected to a channel of a radiation shielding block. A radioactive source assembly, e.g. HDR assembly, which is disposed at a standby position in the channel, is moved to the end portion of the guide tube and positioned a plurality of times at each of a series of preselected positions lying within the end portion of the guide tube. The source assembly is allowed to remain at each of the preselected positions for a plurality of time spaced apart residence times such that each position experiences a plurality of time spaced apart radiations, after which the source assembly is withdrawn from the end portion. The preselected positions and the plurality of residence times are in combination sufficient for the source assembly to produce desired therapeutic radiation of the site of intended therapy, e.g. in a manner which will substantially duplicate the radiation profile of LDR ribbon source assemblies.

In another aspect of the present invention, an apparatus is provided for carrying out the above method. This apparatus provides at least one guide tube having an end portion disposable through at least one orifice in the body and positionable such that the end portion is near the site of intended therapy and an other end is connected to a channel of a radiation shielding block. A radioactive source assembly, e.g. an HDR source assembly, is disposed at a standby position in the channel. Moving means are provided for moving the source assembly from the channel to the end portion. Control means are provided for controlling the functions of the moving means. The control means is capable of: (a) causing the source assembly to be moved from the standby position to the end portion of the guide tube and positioned a plurality of times at each of a series of preselected positions lying within the end portion of the guide tube; (b) allowing the source assembly to remain at each of the preselected positions for a plurality of time spaced apart residence times such that each position experiences a plurality of time spaced apart radiations by the source assembly; and (c) causing the source assembly to be withdrawn from the end portion, e.g. to a rest position such as the standby position in the channel or to another position.

In a further aspect of the above method and apparatus, there are a plurality of guide tubes disposable near the site of intended therapy. In regard to the method, the source assembly is moved, and in regard to the apparatus, the control means is capable of causing the source assembly to be moved, such that the source assembly is moved to the end portion of each guide tube and positioned a plurality of times at each of a series of preselected positions lying in the end portions of each guide tube and allowed to remain at each of the preselected positions for a plurality of predetermined residence times.

Between each time spaced apart residence time, the source assembly is withdrawn from a radiated preselected position to a rest position, e.g. to a standby position in the channel or to another preselected position.

Usually, the source assembly will remain in the rest position after the first residence time and before the second residence time or subsequent residence times for a predetermined rest time. The rest time is a time period between successive radiations of a selected site such that there is a difference in the total biological affect of the radiation on normal cells and cancer cells in the field of radiation, as explained more fully below.

The above method and apparatus provides sequential "pulses" of radiation at each position. Such sequential "pulsed" radiation is continued at each position a plurality of times, with a predetermined rest time between each "pulse", until the cumulative radiation of the total pulses essentially duplicates the total radiation which would have been received at a position by an LDR source continuously remaining at that position for a much longer time or such pulsing can provide patterns of radiation by selection of positions which are revisited a plurality of times and the duration of each pulse therein.

DETAILED DESCRIPTION OF THE INVENTION

Figure 1:
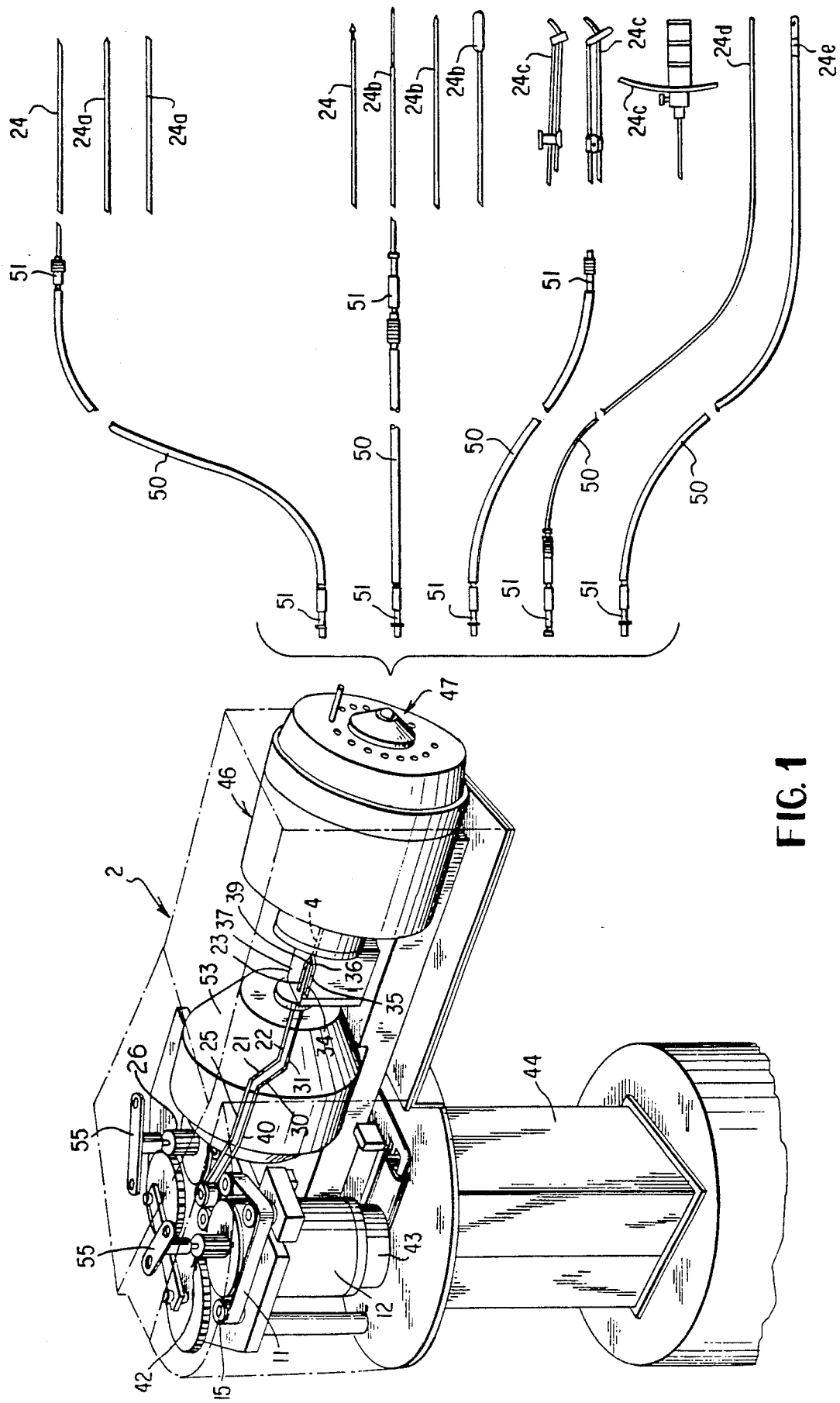
FIG. 1 is a perspective view, partly broken away, showing a preferred embodiment of the apparatus of the invention, where a plurality of branched guide tubes are disposable in the patient for effecting therapy.

FIG. 1 shows a complete embodiment of the present apparatus and in a commercially useful layout. As shown in FIG. 1, the apparatus has a first radioactive source assembly 21 disposed in a first source channel 22. A guide tube 23 is connected at a first end to the first source channel 22 and a second end portion 24 is disposable in the animal body, e.g. a human, for intended therapy. The end portion 24, as shown in FIG. 1, is more usually an applicator, canula or implant needle, e.g. a needle suitable for implantation for the treatment of breast cancer. There is a first source assembly transport thread 25 connected to the first source assembly 21 and to a first source assembly drive means, generally 26, for driving the first source assembly 21 from the first source channel 22 and towards the second end portion 24 of guide tube 4.

Similarly, FIG. 1 shows a further assembly 30 (which may be an LDR source assembly or a "dummy" source assembly) disposed in a further channel 31, and a connector tube 34 connected at a first end 35 to the further channel 31 and at a second end 36 to a connector 37 disposed in guide tube 23 to form a juncture 39 at the connector 37 between the guide tube 23 and the connector tube 34. The connector has a detector therein, as explained in detail in the parent applications. A further assembly transport thread 40 is attached at one end to the further assembly 30 and at the other end to the further assembly drive means, generally 42, which drive means is actuatable for driving the further assembly 30 from the further channel 31 through the connector tube 34 and connector 37 and towards the second end 24 of guide tube 4.

The first source assembly drive means 26 and the further assembly drive means 42 are essentially identical, and as can be seen in connection with further assembly drive means 42, that drive means has a drive motor 12 and power transmitting means for driving the transport thread 40, e.g. a cable, from an appropriate playout spool. Associated therewith are devices for insuring accurate playout of the transport thread, such as belt 11 and rollers 15, the details of which are disclosed in the parent applications. Of course, the drive means also has associated therewith appropriate gearing, journals, switches and stops, as will be appreciated by the art.

While any motor 12 may be used, it is preferable that the motor is a stepping electric motor. As is known in the art, a stepping electric motor turns in stepped increments. While only one motor could be used for driving both the first source assembly drive means and the further assembly drive means, it is preferable that separate stepping motors are independently and operably connected to each of the first source assembly drive means and the further assembly drive means. Since a stepping motor rotates in known step increments, by use of a conventional shaft encoder 43, the degrees of arc (including the number of revolutions of the stepping motor) can be very accurately determined, in a known manner. The shaft encoder 43 generates a signal, and that signal can be fed to a control means 44, e.g. a computer, for determining and/or storing the exact number of revolutions and degrees of arc turned by a stepping motor in driving further assembly 30 from the detector in connector 37 to the site of intended therapy. By using a stepping motor for driving first source assembly 21, and by duplicating the revolutions and degrees of arc used by the stepping motor to move the further assembly from the detector in connector 37 to the site of intended therapy, the control means, e.g. a computer, can very accurately place the first source assembly at the same position as the further assembly had been placed, i.e. at the exact site of intended therapy, as explained in some detail in the parent applications.

However, it has now been found that this same procedure can be used to accurately place the first source assembly 21 at a series of preselected positions lying within the end portion 24 of the guide tube 4. When these preselected positions substantially duplicate the positions which would be occupied by the several discrete sources in a selected length of LDR ribbon placed in end portion 24, and when the source assembly 21 is allowed to remain at each of the preselected positions for predetermined residence times, e.g. to, in total, produce the same or similar affect of radiation as would be produced by LDR sources, each of these positions may be therapeutically radiated by the source assembly 21 in a manner which may substantially duplicate the affects of radiation of an LDR machine.

As noted above, it is often desirable to treat a plurality of intended sites of therapy around a single malignancy, and to this end, the guide tube 4 has a known and conventional indexer means (see U.S. Pat. No. 4,692,628 as an example thereof), generally 46, preferably disposed between the juncture 39 and the second end portion 24 of guide tube 4, and the guide tube is branched at the end of the indexer, generally 47, into a plurality of branched guide tubes 50 attached to the indexer 46. Each of the branched guide tubes has an end portion 24 which may be in a variety of forms, including various applicators and including differently shaped implant needles 24a, specifically conformed tubes 24b, specialized applicator devices 24c, catheters 24d, and special tubes 24e, all of which are known. The end portion 24, therefore, may be in a configuration suitable for the particular malignancy being treated and suitable for the particular orifice through which end portion 24 must either pass or the orifice which must be made by surgery for passage of end portion 24.

Adaptors 51 of various configurations are used for quickly connecting and disconnecting the branched guide tubes 50 to indexer 46 and to the specific configuration of end portion 24. Many such adaptors are known in the art, but of particular and most advantageous use are the adaptors disclosed in U.S. patent application Ser. No. 263,937.

As noted above, indexers are known and need not be described herein, but generally speaking, an indexer functions, by rotation thereof, such that either first guide tube 23 or connector tube 34, through connector 37, can be serially connected to any one of the plurality of branched guide tubes 50. With this arrangement, either the first source assembly or the further assembly is drivable from their respective channels, through the indexer means and toward the end portion 24 of a selected branched guide tube 50, with that selected branched guide tube 50 being selectable by operation of the indexer. The indexer 46 is controlled by the control means 44, e.g. a computer, for controlling the first source assembly and the further assembly drive means and the indexer, in cooperation, such that either assembly may be serially driven to and disposed at the end portion 24 of any selected branched guide tube 50. The control of a conventional indexer 46 by use of a computer for selecting branched guide tubes is known and need not be described herein.

In the present invention, that same control means 44, e.g. a computer, is capable of effecting selected residence times during which the source assembly is disposed and resides at preselected positions in end portion 24 of a selected branched guide tube 50. By controlling the residence times at each of the selected positions in a series of positions, a predetermined regimen of radioactive therapy is providable. Indeed, the control means 44, e.g. a computer, is capable of effecting a selected series of such residence times for each of the positions of the selected series of positions in an end portion 24 and in selected ones of branch guide tubes 50, such that the source assembly may have predetermined first residence times in any selected position in any end portion 24 of any branched guide tube 50 and, likewise, a second or third or further residence times at that same position. Thus, by use of a plurality of time spaced apart residence times at any one position, variations in the total radiation from position to position can be achieved, as well as such variation from the end portion of one branched guide tube to the end portion of another branched guide tube. In order to fully duplicate the radiation pattern of a LDR source, it is often necessary to vary the residence time from positioning of the source assembly to a further time spaced apart positioning of the source assembly at one or more of the preselected positions in a series of preselected positions. Controller 44 is capable of carrying out this function.

Turning now to preferred methods of operation of the apparatus, in one embodiment, the further assembly 30 is driven to the first selected position in end portion 24 of the guide tube 4, and this positioning is confirmed or fine tuned by the physician with use of a fluoroscope or X-ray, since the further assembly is X-ray film imagable. In this case, the further assembly could be a "dummy" (non radioactive) assembly or an LDR source assembly since the radiation therefrom is quite low, and this positioning can be done with minimum radiation exposure. In reaching that first position, a measured excursion of the further assembly from the detector in connector 37 when the further assembly is correctly positioned at the first selected position in end portion 24 is determined. This determination is made by the shaft encoder 43 connected to stepping motor 12, and that determination is fed into and stored by the computer 44. The further assembly may then be withdrawn from the guide tube and into the further assembly channel 31 in shielding block 53 (or some other "resting" position when a "dummy" is used) and the procedure repeated for the second selected position or the further assembly may be moved directly from the first position to a second position. This procedure is repeated for all positions of the series of positions in each guide tube.

Since these positions of the further assembly are stored by computer 44, the computer is now capable of moving the first source assembly, which will usually be an HDR source assembly, for effecting therapy. In this regard, initially the first source assembly 21 will be in a standby position in channel 22, as shown in FIG. 1. The computer will activate the stepping motor and move the first source assembly 21 from that standby position in channel 22 to an end portion of a guide tube and position the first source assembly for the first of a plurality of times at each position of the series of preselected positions lying within end portion 24 of guide tube 4, according to those positions as stored by computer 44. The computer 44 will also allow that first source assembly 21 to remain at each of the preselected positions for a predetermined first residence time and succeeding residence times. The first residence time and any succeeding residence times in any one of the preselected positions may be the same or different from the first residence time and any succeeding residence times of any of the other preselected positions, and the particular residence time for each of the plurality of residence times at each position will be determined by the physician, based on the particular malignancy involved, in order to therapeutically radiate the malignancy by that first source assembly.

The first source assembly, after a "rest" time as described more fully below, will be moved by computer 44 to that same position of the preselected positions for a second residence time or third or fourth or further residence times. The computer 44 will control the movement and residence times of the first source assembly to effect these further residence times in the selected position or positions.

After the desired regimen of radiation at all of the positions of all of the end portions 24 is accomplished, the first source assembly 21 is withdrawn from an end portion 24 back to the standby position in channel 22.

The preselected positions and the predetermined residence times, as both being selected by the physician, are in combination sufficient for the first source assembly to produce the desired therapeutic radiation of the site of intended therapy, and by specifically selecting the positions, residence times (which may vary with succeeding residence times at any one position and from position to position), and number of residence times (which may vary from position to position), that radiation may be made to, substantially, duplicate the radiation which would have been achieved by an LDR source ribbon or ribbons lying in one or more of end portions 24 or to effect a desired radiation pattern essentially the same as an LDR pattern or a more beneficial pattern than that of an LDR source pattern, as more fully explained below.

This also provides wide latitude for the physician in selecting the regimen of radiation. Thus, in one embodiment, after the source assembly remains at a position for a predetermined residence time, the source assembly is then moved from that radiated position to another position of the series of positions and allowed to remain at that position for, again, a predetermined residence time. In other words, the source assembly is stepped, in sequence or in some other order, through all of the positions of the series of positions in one of the branched guide tubes 50 and allowed to remain at each of those positions for the predetermined residence times, before the source assembly is withdrawn from that branched guide tube and returned to the shielding block.

On the other hand, the source assembly may remain at the positions for the predetermined residence times, and then the source assembly is withdrawn therefrom to a rest position, e.g. to the standby position in the channel 22. Thereafter, the source assembly is again subsequently moved from that rest position to at least some of the preselected positions of the series of positions and allowed to remain at those positions for, again, predetermined residence times. Thus, the source assembly is at "rest" in the standby position between radiation of different positions in the series of positions. Indeed, the source assembly may remain at rest in the standby position for a predetermined rest time between successive radiations at the same position of the series of positions in a guide tube. The time interval at the rest position may be important for certain regimens, particularly in regard to the "repair time" of cancer cells, as explained more fully hereinafter. Thereafter, succeeding residence times at that position or other positions are achieved in a similar manner.

As noted above, most often there will be a plurality of guide tubes 50 disposed near the site of intended therapy and the source assembly 21 is moved to each of a series of preselected positions lying in the end portion 24 of each guide tube. The source assembly, again, will be allowed to remain at each of the preselected positions for a predetermined first residence time and for succeeding residence times, i.e. the source assembly is positioned a plurality of times at each of a series of preselected positions lying in the end portion of each guide tube and allowed to remain at each of the positions for a plurality of predetermined residence times. Thus, with the plurality of branched guide tubes 50 in and around the malignancy and with the preselected positions in each end portion 24 of each branched guide tube 50, along with the predetermined residence times at each of those positions in each branched guide tube, a total regimen of radiation for effective therapy can be provided. That therapy can, substantially, duplicate the radiation therapy of LDR source ribbons that are disposed in the end portion 24 of each of the plurality of branched guide tubes 50 or effect a more beneficial pattern, as explained in more detail below. Here again, depending upon the selected regimen of radiation, the source assembly may be moved to each of the preselected positions in each of the end portions of the guide tubes 50 in a selected order. That selected order may be such that the source assembly is moved to each of the preselected positions in a branched guide tube 50 and then moved to preselected positions in another branched guide tube 50. Alternatively, however, the selected order may be such that the source assembly is moved to less than each of the preselected positions in a selected branched guide tube, and then the source assembly is moved to a preselected position or positions in another selected branched guide tube 50. Of course, with this order, eventually, the source assembly would be moved back into the branched guide tubes where all of the preselected positions had not been radiated for radiation of those unradiated positions or for further radiation of a previously radiated position.

It can thus be seen from the above that a wide latitude of radiation is provided by the present invention, and that radiation may be selected in such a manner that the radiation substantially duplicates the radiation achieved by LDR source assemblies. Alternatively, the steps of the method may be periodically repeated, whereby the cumulative radiation of repeated radiation at one or more of the sites of intended therapy is sufficient that each of the positions are therapeutically radiated by the source assembly to cumulatively form a predetermined pattern of radiation which is different from but superior to the pattern of radiation of LDR source assemblies.

In this latter regard, it has been discovered that an advantage can be obtained by repeating the above-described radiation procedure only after a "rest time" between successive radiations. The term "rest time" is used in this specification as a convenient name for a time period which is determined by a complex set of conditions affecting radiation therapy. Basically, the "rest time" period is such that utilization is made of the differences in "repair rates" (and hence "repair times") between normal tissue cells and cancer cells. For example, the "rest time" between successive radiations may be such that successive radiations affect the cancer cells in a manner substantially equivalent to LDR continuous radiation, but also such that the "rest times" provide for some "repair" of normal cells between successive radiations. The ideal radiation (and successive radiations) is where there is maximum damage to cancer cells and minimum damage to normal cells. The ratio between the damage to normal cells and the damage to cancer cells can be called the "therapeutic ratio" (or gain). This ratio should be as large as possible, and it is known in the art that the ratio can be affected by the dose (or intensity) of the radiation and the time of radiation, as well as the number of separate sessions of radiation (a total desired amount of radiation is often given in separate sessions). However, especially, the dose and time considerations constitute complex functions that express the interdependency of these two, as well as the number of sessions of treatment, in producing a total biological effect on a given volume of cells (having both normal and cancer cells). This concept is, thus, based on the fact that cancer tissue and healthy normal tissue respond differently when being exposed to radiation.

More generally, this holds for all tissues and can be related to the following factors:

1. Each tissue type can be characterized by individual parameters describing:
intrinsic radiosensitivity
capability and speed of repairing sublethal radiation damage (repair capacity and kinetics)
repopulation activity
redistribution of cells throughout the cell cycle
reoxygenation 2. The interplay of these basic parameters leading to the tissue specific irradiation response is determined by the manner in which a total radiation dose is administered in time-dose patterns (dose fractions given in time intervals).

Several formulas, or mathematical models, have been created to at least partially explain the above various relationships. However, these mathematical models are beyond the scope of this specification and are not necessary for a description of the invention. Nevertheless, those skilled in the art will appreciate the significance of the term "rest time" from the above explanation.

For purposes of this specification, "rest time" may be simplified to a time period between successive radiations of a selected site such that there is a difference in the total biological affect of the radiation on normal cells and cancer cells in the effective field of radiation, i.e. there is a difference in the overall survival of normal cells as opposed to cancer cells during the course of radiation treatment. This consideration is referred to in this specification as cell "repair time", but it is to be understood that these terms are but convenient names for the more complex considerations described above.

The repair time of cells, in general, varies considerably, but most healthy cells, in connection with which malignancies most often occur, have repair times of less than about 6 hours, and therefore, preferably, the procedure is repeated at least within a 6-hour period, i.e. the "rest" time is no greater than 6 hours. Often, these repair times are much shorter, and in those cases, the procedure is repeated (after the "rest" time) within about an every 30 minutes to 4-hour period, e.g. within about 1 to 3 hours, especially 1 to 1 ½ hours.

For illustration purposes of the foregoing, it can be assumed that healthy cells surrounding a cancer have a "repair time" of one hour from a sublethal radiation. It can be further assumed that the involved cancer cells have a "repair time" of six hours. Thus, if cells are radiated in a plurality of sublethal "pulses" of radiation with at least one hour "rest time" between "pulses" but less than six hours "rest time" between "pulses", overall the healthy cells will continue to survive, while the cancer cells will continue to be damaged to destruction.

This technique can be referred to as "pulsed dose rate" (PDR) radiation, and when conducted with brachy radiation therapy can have a very marked beneficial result in terms of effective radiation therapy. In one aspect, PDR radiation can very closely approximate the radiation effects of low dose rate (LDR) radiation. Low dose rate (LDR) treatments (e.g. 150 cGy/h) can be thought as fractionation schedules with an ultimate time-dose pattern: very small doses are given continuously. From the radiobiological point of view, such exploits the difference in repair ability between normal tissue and tumor tissue, since most tumors have a poorer repair capacity than normal tissues and, therefore, do not recover from radiation damages as well as normal tissue does.

Additionally, since LDR treatments are applied interstitially or intracavitary, they allow a more tumor orientated, physical dose deposition as compared to external beam irradiation. Therefore, it is possible to adjust the radiation dose so that the maximum amount is given to the tumor rather than to normal tissue.

Figure 2:
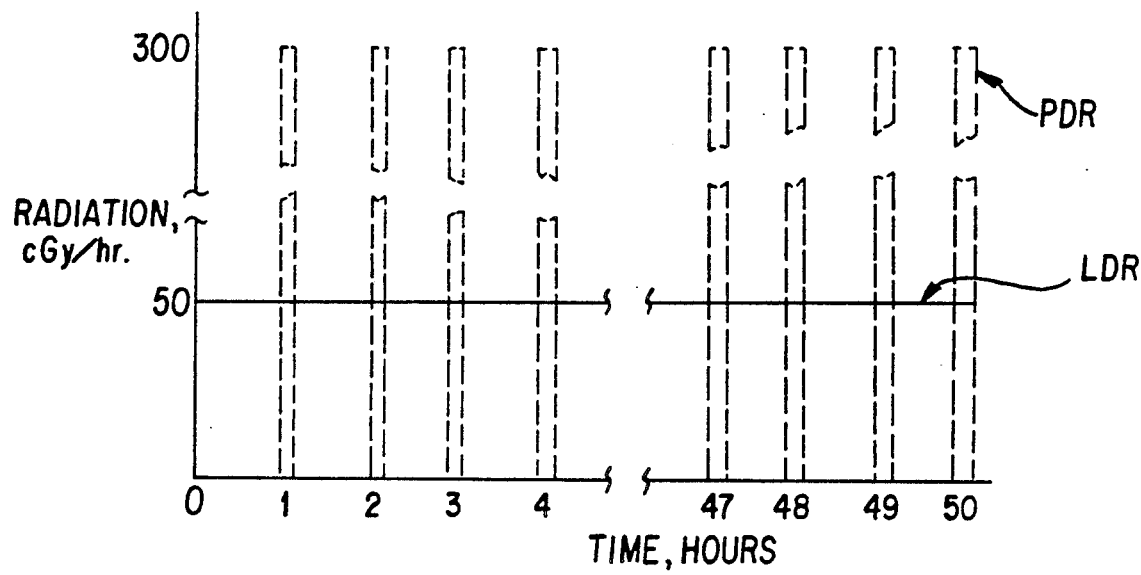
FIG. 2 is a diagrammatic graph of the effects of "pulsed" radiation.

In pulsed dose rate (PDR) radiation, for example with a medium dose rate (MDR) source, the continuous LDR treatment is replaced by a sequence of pulses given interstitially, but separated by a "rest time" period. FIG. 2 illustrates this effect. In FIG. 2, the solid line indicates a typical low dose rate (LDR) radiation where radiations of 50 cGy/Hr are continuously administered for 50 hours, i.e. 2500 cGy in total. The dashed lines indicate pulsed dose rate (PDR) radiation where 300 cGy/Hr are pulsed every hour for about ten minutes, i.e. leading to 50 cGy in one hour and 50 pulses are used. The total radiation dose of 2500 cGy given by both the LDR and PDR treatment is a typical dose for brachytherapy. From the radiological point of view, a change of fractionation schedules, as described above, will lead to an equivalent radiobiological response for a wide variety of human cell lines. Thus, the PDR radiation can very closely approximate the LDR radiation in this regard.

However, in another aspect, the PDR radiation has several other distinct advantages over LDR radiation. First, between pulses, the patient is free to move and may disconnect from the remote after-loading machine, which greatly increases patient comfort, as opposed to the LDR radiation where the patient must be connected to the LDR machine for up to 50 hours or more (or if disconnected, the therapy is interrupted and careful accountings for such interruptions must be made).

Secondly, since the repair time for healthy cells is, usually, less than five or six hours, during the PDR radiation, as opposed to LDR radiation, healthy cells tend to recover from the radiation, while cancer cells, with a repair time of typically about six hours or more, do not recover and continue to be damaged to destruction.

Thirdly, as opposed to a stationary LDR source during the therapy, the PDR source can be changed in the positions of radiation and the duration of radiation to produce a desired pattern of radiation. For example, in treating prostate cancer, with LDR radiation, a ribbon of LDR sources is placed in needles implanted in and around the prostate. However, the prostate lies close to the bladder on one side and close to the rectum on the other side. Since the amount of radiation received by tissue follows the inverse square law, in order to sufficiently irradiate the prostate, the bladder and rectum lying close to the prostate can easily receive an amount of radiation which can perforate either, with extremely undesired results.

Another important advantage of the present pulse radiation is in regard to uniformity of time spaced apart radiation treatments. In some regimens, it is desired that the radiation treatments of a particular patient suffering from a particular cancer be in time spaced apart treatments, which are referred to as sessions. The time interval between sessions may be only part of a day, e.g. 12 hours, or may be a few days, or a week, or even several weeks or more. Particularly in regard to more complicated cancers, the positions for placing the radioactive source and the residence time for any one pulse (pulse width) at any one of multiple such positions is time consuming and difficult to calculate for the radiologist. However, in the time intervals between sessions, the radiation source loaded into an afterloading machine will decay and the intensity of that source, correspondingly, decreases. For example, with iridium sources, the half life of the source is only about 74 days. Thus, if sessions are spaced apart, for example, by one week, then a significant decay of the source will occur during that period, and the intensity of the radiation for the treatment performed one week later, will be significantly reduced. While the regimen of treatment can be recalculated for the second, one week spaced apart session, that calculation is time consuming and the decrease in intensity of radiation can require different positionings of the radiation source. This, therefore, constitutes a substantial problem in administering radiation for therapeutic purposes in time spaced apart regimens.

The present pulsed radiation, however, can obviate most of the difficulty in that regard. Since the amount of radiation received by the patient with any one pulse at any one preselected position is dependent upon the intensity of radiation of the radioactive source and the time period (pulse width) of the pulse, the decrease in radioactive intensity of the source, occasioned by decay of the source, can readily be compensated by correspondingly lengthening the time of the pulse of the radiation. Therefore, by simply adjusting the time of the pulse (pulse width) of the radiation, as the radioactive source decays, compensation can be easily made for that decay, without substantial recalculation by the physicist or radiotherapist of the regimen and, usually, without the necessity of providing additional preselected sites of radiation. This provides a very significant and substantial advantage to the art in radiation therapy, when that therapy is carried out at time spaced apart sessions. Indeed, the controller, e.g. computer 44, can easily be programmed for automatically compensating for the decay of the source, when time spaced apart sessions are to be used, and it is therefore easy for the person administering the radiation to deliver the desired radiation at each of the preselected sites even when the source has decayed during a time interval between radiation sessions.

Figure 3:
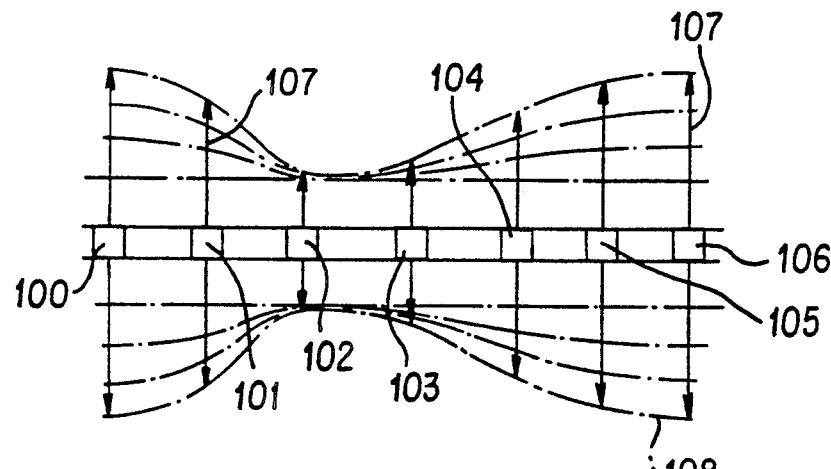
FIG. 3 is a diagrammatic illustration of patterns of radiation which are achievable with "pulsed" radiation.

With PDR radiation, the radiation can be formed into a desired pattern. FIG. 3 illustrates this effect. In that figure, a plurality of PDR radiation sites 100 to 106 are selected for a particular cancer, for example prostate cancer. However, the total radiation at any one site is dependent on the intensity of the radiation source, the number of times that source is "pulsed" at that site, and the pulse width (duration of each pulse). If one assumes that the bladder and rectum lie near sites 102 and 103, then the radiation of those sites can be diminished, as compared with other sites, i.e. sites away from the bladder and rectum, by decreasing the number of pulses given at sites 102 and 103 and/or decreasing the duration of pulses at those sites. The vertical arrows 107 represent the total radiation so received at each site, and the total radiation field or pattern is represented by background lines 108.

Thus, with PDR radiation, by adjusting the location of pulse sites, the number of pulses given at each site, and the duration of each pulse at each site, almost any desired pattern of radiation can be produced. With such patterns, effective brachy radiation therapy can be conducted to destroy cancer cells but largely avoid damage or destruction of closely adjacent healthy cells, which is a very substantial benefit to the art.

It will also be appreciated from the above that a wide latitude exists for the number of pulses and duration of pulses. For example, the number of pulses at any one site could be from as little as only two, where radiation is to be very minimal, e.g. a site near a sensitive organ, to as many as 140 or 150 or more, e.g. well within a massive cancer, but more usually the number of pulses will be 3 or 4 to 40 or 70, e.g. 10–30 pulses. The duration of a pulse, depending on the particular radiation source, could be from as little as 0.5 second, for very near a sensitive organ, to 20 minutes, for inside a massive cancer, but more usually the duration will be no more than 20 minutes, e.g. 10 minutes, and more usually from 1 second to 120 seconds. The total residence time for all pulses at any one position can be from 1 second to 60 minutes or greater but will usually be between 10 and 40 minutes.

The "rest time" between pulses can also vary widely depending on the repair time of the surrounding healthy cells and the treated cancer cells. However, a pulse should be repeated at least every 6 hours, e.g. at least every 4 hours, and more usually about once every 30 minutes or once every 1 to 1 ½ hours, especially to duplicate LDR radiation.

Normally, the rest position will be the standby position in the channel, since the rest time will be so long that the first source assembly cannot be moved to one or more other positions for required residence times at those positions to occupy the entire rest time. However, with multiple guide tubes and multiple residence times at multiple positions, the rest position may be simply the position of the first source assembly at a position or positions away from the particular position for which the rest time is appropriate.

The controller 44, e.g. a computer, also allows the use of automatic safety controls. For example, if during treatment, the detector in connector 37 detects movement of the transport thread, e.g. the patient has tampered with the implant needle or a guide tube, then the computer can cause an automatic withdrawal of the source assembly back into shielding block 53. Likewise, in the event of a power failure, the computer can withdraw the source assembly back into shielding block 53 by use of a safety backup battery (now shown in the drawings).

All of the above provides a very substantial advantage to the art, and it will be understood that many modifications of the above-described invention will be apparent to those skilled in the art, and it is intended that those modifications be embraced by the spirit and scope of the annexed claims.

What is claimed is:

1. A method for effecting radiation therapy of a site of intended therapy in an animal body comprising:
   (1) placing at least one guide tube through at least one orifice in the body such that an end portion of the guide tube is disposed near the site of intended therapy;
   (2) connecting an other end of the guide tube to a channel of a radiation shielding block;
   (3) moving a radioactive source assembly, and controlling the movement thereof with a computer, such that the source assembly is moved from a standby position toward said end portion of the guide tube and positioning the source assembly a plurality of times at each of a series of preselected positions lying within the guide tube and allowing the source assembly to remain at each of the preselected positions for a plurality of time spaced apart variable residence times such that each position experiences a plurality of time spaced apart variable radiations by said source assembly; and
   (4) withdrawing the source assembly from said guide tube; and
   wherein said preselected positions and the plurality of residence times at each preselected position are in combination sufficient for the source assembly to produce therapeutic radiation of the site of intended therapy.

2. The method of claim 1 wherein after the source assembly remains at one of said preselected positions for a predetermined residence time, the source assembly is moved from that radiated preselected position to another preselected position of the series of said preselected positions and allowed to remain at said another preselected position for a predetermined residence time.

3. The method of claim 1 wherein after the source assembly remains at one of said preselected positions for a predetermined residence time, the source assembly is withdrawn therefrom to a rest position, and the source assembly is again subsequently moved from the rest position to that same preselected position and allowed to remain at that same preselected position for a predetermined further residence time.

4. The method of claim 3 wherein the source assembly remains at the rest position for a predetermined rest time.

5. The method of claim 4 wherein the rest time is a time period between successive radiations of a selected site such that there is a difference in total biological affect of the radiation on normal cells and cancer cells in the effective field of radiation.

6. The method of claim 5 wherein the rest time is in the range of at least thirty minutes to no more than six hours.

7. The method of claim 1 wherein there are a plurality of guide tubes disposed near the site of intended therapy and the source assembly is moved toward the end portion of each guide tube and positioned a plurality of times at each of a series of preselected positions lying in each guide tube and allowed to remain at each of the preselected positions for a plurality of predetermined residence times.

8. The method of claim 7 wherein the source assembly is moved to each of the preselected positions in each of the guide tubes in a selected order.

9. The method of claim 8 wherein the selected order is such that the source assembly is moved to each of the preselected positions in one of said guide tubes and then the source assembly is moved to other preselected positions in another of said guide tubes.

10. The method of claim 8 wherein the selected order is such that the source assembly is first moved to less than each of the preselected positions in a first of said guide tubes and then the source assembly is moved to a preselected position in another of said guide tubes and then the source assembly is moved to a preselected position in the first guide tube.

11. The method of claim 7 wherein after the source assembly remains at one of said preselected positions for a said predetermined residence time, the source assembly is withdrawn therefrom to a rest position, and the source assembly is again subsequently moved from the rest position to that same said preselected position and allowed to remain at that same said preselected position for a predetermined further residence time.

12. The method of claim 11 wherein the source assembly remains in the rest position for a predetermined rest time.

13. The method of claim 12 wherein the rest time is a time period between successive radiations of a selected site such that there is a difference in total biological affect of the radiation on normal cells and cancer cells in the effective field of radiation.

14. The method of claim 13 wherein the rest time is in the range of at least thirty minute to no more than six hours.

15. The method of claim 1 wherein the animal body is a human body.

16. The method of claim 1 wherein the source assembly is moved by a transport thread driven by a stepping motor.

17. The method of claim 1 wherein the source assembly is a high dose rate source assembly.

18. The method of claim 1 wherein any one residence time is at least one second and up to 120 seconds.

19. The method of claim 18 wherein the total residence times are between 10 and 40 minutes.

20. An apparatus for effecting radiation therapy of a site of intended therapy in an animal body comprising:
   (1) a radiation shielding block having a channel therein;
   (2) at least one guide tube having an end portion disposable through at least one orifice in the body and positionable such that the end portion is near the site of intended therapy and an other end is connected to said channel of the radiation shielding block;
   (3) a radioactive source assembly disposed at a standby position in said channel;
   (4) moving means for moving the source assembly from said channel toward said end portion;
   (5) computer control means for controlling the moving means, which control means performs functions:
      (a) causing the source assembly to be moved from the standby position toward the end portion of the guide tube and positioned a plurality of times at each of a series of preselected positions lying within the guide tube such that preselected positions are radiated;
      (b) allowing the source assembly to remain at each of the preselected positions for a plurality of time spaced apart variable residence times such that each position experiences a plurality of time spaced apart variable radiations by said source assembly; and
      (c) causing the source assembly to be withdrawn from said guide tube.

21. The apparatus of claim 20 wherein the control means performs functions of causing the sources assembly to be moved from a radiated preselected position to an unradiated preselected position of the series of positions and allowing the source assembly to remain at each unradiated position for a predetermined residence time.

22. The apparatus of claim 20 wherein the control means performs functions of causing the source assembly to be withdrawn from a radiated position to a rest position, and subsequently causing the source assembly to be again moved from the rest position to that same said radiated position and allowing the source assembly to remain at that same said radiated position for a predetermined further residence time.

23. The apparatus of claim 22 wherein the control means performs the function of causing the source assembly to remain at said rest position for a predetermined rest time.

24. The apparatus of claim 23 wherein the rest time is a time period between successive radiations of a selected site such that there is a difference in total biological affect of the radiation on normal cells and cancer cells in the effective field of radiation.

25. The apparatus of claim 24 wherein the rest time is in the range of at least thirty minutes to no more than six hours.

26. The apparatus of claim 20 wherein there are a plurality of said guide tubes and the control means performs the functions of causing the source assembly to be moved toward the end portion of each guide tube and positioned a plurality of times at each of a series of preselected positions lying in each guide tube and allowing the source assembly to remain at each of the preselected positions for a plurality of predetermined residence times.

27. The apparatus of claim 26 wherein the control means performs the function of causing the source assembly to be moved to each of the preselected positions in each of the guide tubes in a selected order.

28. The apparatus of claim 27 wherein the control means performs the function of causing the source assembly to be moved in the selected order such that the source assembly is moved to each of the preselected positions in each of said guide tubes and then moved to other preselected positions in another of said guide tubes.

29. The apparatus of claim 27 wherein the control means performs functions of causing the source assembly to be first moved to less than each of the preselected positions in a first of said guide tubes and then moved to a preselected position in another of said guide tubes and then moved to a preselected position in the first guide tube.

30. The apparatus of claim 26 wherein the control means performs functions of causing the source assembly to be withdrawn from said preselected position in one of said guide tubes to a rest position, and subsequently causing the source assembly to be moved from the rest position to the same said preselected position and allowed to remain at that same said preselected position and allowed to remain at that same said preselected position for a predetermined further residence time.

31. The apparatus of claim 30 wherein the control means performs the function of causing the source assembly to remain at said rest position for a predetermined rest time.

32. The apparatus of claim 31 wherein the rest time is a time period between successive radiations of a selected site such that there is a difference in total biological affect of the radiation on normal cells and cancer cells in the effective field of radiation.

33. The apparatus of claim 32 wherein the rest time is in the range of at least thirty minutes to no more than six hours.

34. The apparatus of claim 20 wherein the control means performs the function of moving the source assembly to one of said preselected positions from 1 to 140 times.

35. The apparatus of claim 20 wherein the moving means includes a stepping motor and a transport thread, and the transport thread is attached at one end thereof to the source assembly and at the other end thereof to said stepping motor.

* * * * *